United States Patent
Levi

(10) Patent No.: US 8,726,902 B2
(45) Date of Patent: May 20, 2014

(54) SYSTEM AND METHOD FOR SMART DELIVERY OF BACKUP BREATHS

(75) Inventor: Andrew Phillip Levi, Madison, WI (US)

(73) Assignee: General Electric Company, Schenectady, NY (US)

( * ) Notice: Subject to any disclaimer, the term of this patent is extended or adjusted under 35 U.S.C. 154(b) by 1226 days.

(21) Appl. No.: 12/138,605

(22) Filed: Jun. 13, 2008

(65) Prior Publication Data
US 2009/0308394 A1    Dec. 17, 2009

(51) Int. Cl.
*A61M 16/00* (2006.01)
*A62B 7/00* (2006.01)
*F16K 31/02* (2006.01)

(52) U.S. Cl.
USPC ..................................... 128/204.21; 137/908

(58) Field of Classification Search
USPC ............. 128/204.21, 204.18, 204.23, 200.24, 128/204.22, 204.26–204.28, 128/205.23–205.24, 206.21, 128/206.28–206.29, 207.12, 128/207.14–207.18, 898; 137/908
See application file for complete search history.

(56) References Cited

U.S. PATENT DOCUMENTS

| | | | |
|---|---|---|---|
| 4,003,377 A * | 1/1977 | Dahl | 128/204.23 |
| 6,213,119 B1 | 4/2001 | Brydon et al. | |
| 6,305,374 B1 * | 10/2001 | Zdrojkowski et al. | 128/204.21 |
| 6,484,719 B1 * | 11/2002 | Berthon-Jones | 128/204.23 |
| 7,255,103 B2 | 8/2007 | Bassin | |
| 7,347,205 B2 * | 3/2008 | Levi | 128/204.18 |
| 7,484,508 B2 * | 2/2009 | Younes | 128/204.18 |
| 7,549,421 B2 * | 6/2009 | Levi et al. | 128/204.21 |
| 2004/0231670 A1 * | 11/2004 | Bassin | 128/204.18 |
| 2005/0056283 A1 * | 3/2005 | Levi et al. | 128/204.21 |
| 2006/0070624 A1 * | 4/2006 | Kane et al. | 128/204.23 |
| 2007/0044798 A1 * | 3/2007 | Levi | 128/204.23 |
| 2008/0302364 A1 * | 12/2008 | Garde et al. | 128/204.23 |

* cited by examiner

*Primary Examiner* — Tan-Uyen T Ho
*Assistant Examiner* — Mark K Han
(74) *Attorney, Agent, or Firm* — Andrus Intellectual Property Law, LLP

(57) ABSTRACT

A method for delivering ventilatory support to a patient is presented. The method includes controlling delivery of a first backup breath by delaying onset of the first backup breath, wherein delaying the onset of the first backup breath is configured to allow selection of an appropriate backup rate. Systems and computer-readable medium that afford functionality of the type defined by this method is also contemplated in conjunction with the present technique.

13 Claims, 4 Drawing Sheets

SYSTEM AND METHOD FOR SMART DELIVERY OF BACKUP BREATHS

BACKGROUND

This disclosure relates generally to clinical workflow, and more particularly to a design of a method configured to aid in enhancing clinical workflow.

In a caregiving facility, such as a hospital, and more particularly, in an Intensive Care Unit (ICU), it may be desirable to provide artificial ventilation to a majority of patients. Patients are ventilated in order to treat and manage respiratory failures, such as asthma, pneumonia, pulmonary edema, pulmonary embolism, chronic bronchitis, post-operative hypoxemia, chest injuries and chronic lung disease. Along with patients suffering from respiratory failure, certain patients may need ventilatory support for other medical reasons. By way of example, post-operative ICU patients and certain maxillofacial surgical patients may also require a period of post operative care/management in the ICU, during which time the patients are typically kept sedated and ventilated.

Traditionally, artificial ventilation is provided via use of a ventilator. More particularly, artificial ventilation is provided via positive pressure ventilation, where gas is delivered under positive pressure, allowing alveoli expansion and gas exchange. It may be noted that artificial ventilation may include invasive ventilation, non-invasive ventilation, or a combination thereof. Once a patient has been identified as needing invasive ventilation, the patient may be intubated and placed on a ventilator and ventilated using positive pressure.

Alternatively, the patient may be non-invasively ventilated. Non-invasive ventilation may be used to refer to the delivery of mechanical ventilation using a facemask or other similar devices as opposed to the use of an endotracheal tube in invasive ventilation. Non-invasive ventilation (NIV) is being increasingly used to circumvent complications caused by invasive ventilation, such as infections and/or airway trauma.

As will be appreciated, during artificial ventilation, such as NIV, the patient may stop breathing for a period of time. Spontaneously breathing patients may often breathe in an accelerated fashion and slow their breathing or even temporarily pause breathing. There are specific clinical conditions such as Cheynes-Stokes breathing that result in amplification of this type of breathing. It may be desirable to deliver backup breaths if this period exceeds a predetermined period of time, where the predetermined period of time may include a backup rate.

Currently available techniques that implement a backup rate unfortunately account for these varying breathing patterns in a sub-optimal manner. More particularly, the currently available techniques are intolerant of pauses in the breathing patterns of patients as these techniques are configured to deliver the initial backup breath exactly one breath period after the last trigger. Furthermore, the implementation of the backup breaths in the presently available techniques disadvantageously results in clinicians setting the backup rate to a very low value. This increases the chance of patients becoming asynchronous with the ventilator or getting unneeded and uncomfortable backup breaths. Moreover, if the patient truly becomes apneic and stops breathing, presently available techniques will not deliver a sufficient number of backup breaths for proper ventilation.

It may therefore be desirable to develop a design of a method that may be configured to advantageously aid in the smart delivery of backup breaths, thereby minimizing patient discomfort and enhancing clinical workflow. More particularly, it may be desirable to delay the onset of a first backup breath, thereby allowing the patient to temporarily pause breathing.

BRIEF DESCRIPTION

In accordance with aspects of the present technique, a method for delivering ventilatory support to a patient is presented. The method includes controlling delivery of a first backup breath by delaying onset of the first backup breath, wherein delaying the onset of the first backup breath is configured to allow selection of an appropriate backup rate. Computer-readable medium that afford functionality of the type defined by this method is also contemplated in conjunction with the present technique.

In accordance with further aspects of the present technique, a system for delivering ventilatory support to a patient is presented. The system includes a ventilation system configured to provide artificial respiration to the patient, wherein the ventilation system is operationally coupled to the patient via a patient interface. In addition, the system includes a backup breath delivery module configured to automatically control delivery of a first backup breath by delaying onset of the first backup breath, wherein delaying the onset of the first backup breath is configured to allow selection of an appropriate backup rate.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
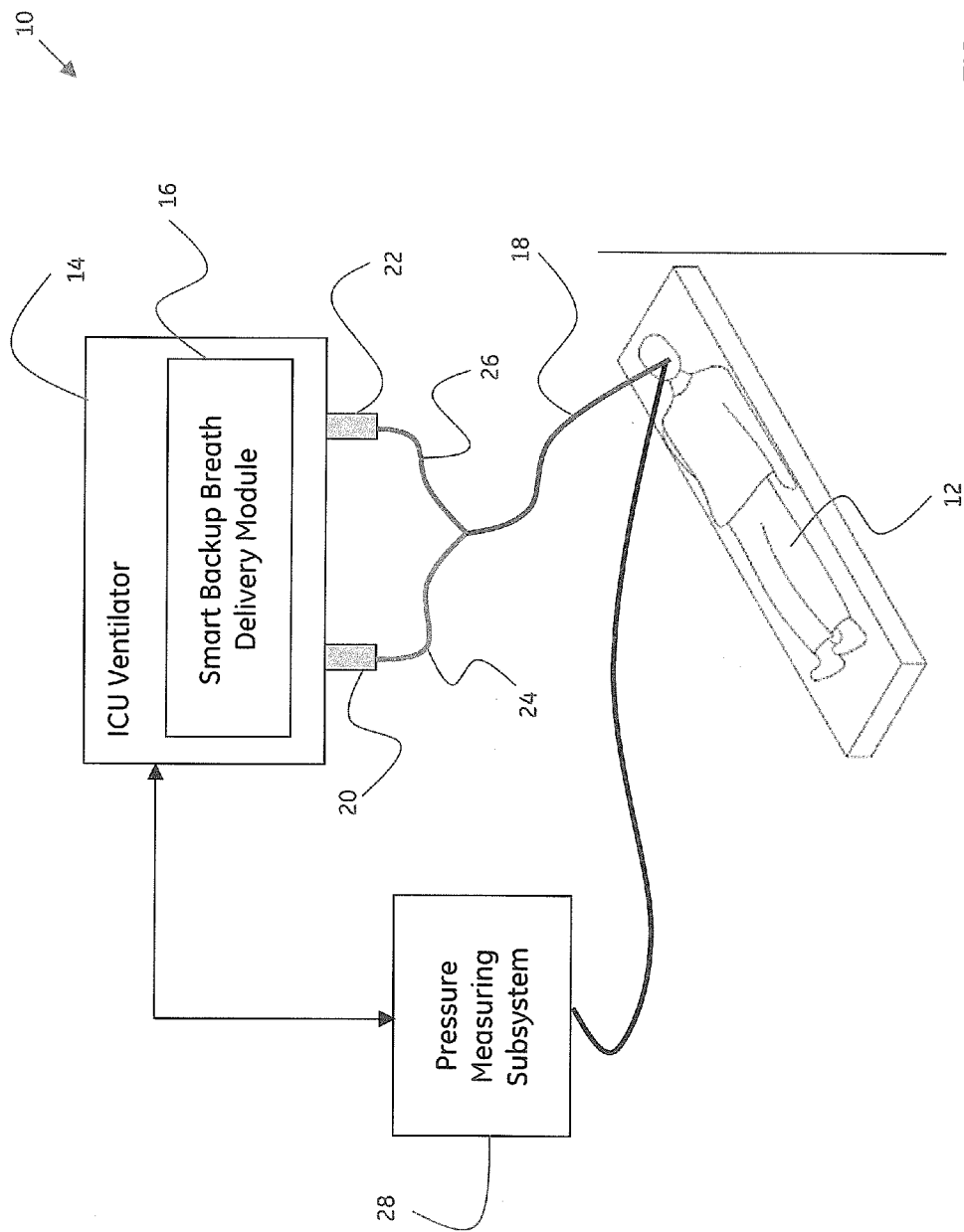
FIG. 1 is a block diagram of a ventilation system configured to deliver ventilatory support to a patient, in accordance with aspects of the present technique.

FIG. 1 is a block diagram of an exemplary ventilation system 10 that may be configured to aid in delivering ventilatory support to a patient 12, in accordance with aspects of the present technique. In other words, the exemplary ventilation system 10 may be configured to aid a traditional ICU ventilator in smart delivery of ventilatory support to the patient 12, thereby enhancing clinical workflow and minimizing discomfort to the patient 12.

The ventilation system 10 may generally be operationally coupled to the patient 12 via a patient interface 18. It may be noted that the patient interface 18 may include an invasive patient interface, a non-invasive patient interface, or a combination thereof. By way of example, the invasive patient interface may include a breathing tube. The breathing tube may be inserted through the nose or mouth of the patient 12 and advanced into the patient's airway until the breathing tube passes through the patient's larynx. Examples of the non-invasive patient interface may include a face mask.

Furthermore, in FIG. 1, the ventilation system 10 is shown as being operationally coupled to the patient 12. In one embodiment, the ventilation system 10 may include a ventilator 14, such as an ICU ventilator. As will be appreciated, the ICU ventilator 14 is a machine that may be configured to aid the patient 12 in breathing through a patient interface 18, where the patient interface 18 is operationally coupled to the ICU ventilator 14. Further, the ICU ventilator 14 may also include a first connector 20 and a second connector 22. The first connector 20 and the second connector 22 may be configured to aid in operationally coupling the ICU ventilator 14 to the patient 12 via the patient interface 18.

As noted hereinabove, the patient 12 may be operationally coupled to the ICU ventilator 14 via the patient interface 18. The patient interface 18 may include an inspiratory branch 24 and an expiratory branch 26. In the embodiment illustrated in FIG. 1, the patient interface 18 is shown as being operationally coupled to the first connector 20 of the ICU ventilator 14 via the inspiratory branch 24. The ICU ventilator 14 may be configured to pump gas into the lungs of the patient 12 through the inspiratory branch 24. In a similar fashion, the patient interface 18 is also shown as being operationally coupled to the second connector 22 of the ICU ventilator 14 via the expiratory branch 26. The ICU ventilator 14 may be configured to aid in the exhalation of gas from the lungs of the patient 12 through the expiratory branch 26.

As will be appreciated, there exist several variations in the breathing pattern of the patient 12. For example, the patient may breathe fast, slow his/her breathing, pause his/her breathing, stop breathing, or a combination thereof. Generally, the presently available techniques fail to allow pauses in the breathing patterns of a patient 12 as these techniques are configured to deliver a first backup breath exactly one breath period after the last trigger. Consequently, backup breaths may be unnecessarily delivered to the patient 12, thereby enhancing patient discomfort. Accordingly, a module configured to advantageously aid a traditional ventilation system in the delivery of smart ventilatory support, is presented.

In accordance with aspects of the present technique, the shortcomings of the presently available techniques may be circumvented via use of an exemplary smart backup breath delivery module 16. In the embodiment illustrated in FIG. 1, the ICU ventilator 14 may be shown as including the smart backup breath delivery module 16, where the smart backup breath delivery module 16 is configured to aid the ICU ventilator 14 in delaying onset of a first backup breath to the patient 12. More particularly, the smart backup breath delivery module 16 may be configured to use a previous breath period to delay the onset of the first backup breath to the patient 12.

Further, in a presently contemplated configuration, the ICU ventilator 14 is shown as including the smart backup breath delivery module 16. However, in certain other embodiments, the smart backup breath delivery module 16 may include a standalone module configured for use with a ventilation system, such as the ventilation system 10 (see FIG. 1). The working of the smart backup breath delivery module 16 will be described in greater detail with reference to FIGS. 3-4.

In addition, the ventilation system 10 may also include a pressure measuring subsystem 28, where the pressure measuring subsystem 28 may be configured to aid in measuring pressure of air that is pumped into the patient 12. It may be noted that in certain embodiments, an additional pressure measuring subsystem (not shown in FIG. 1) may be employed to aid in measuring the pressure of air on the breathing tube side.

As described hereinabove, currently available techniques that implement a backup rate are unfortunately intolerant of pauses in the breathing patterns of the patient 12 and account for these variations in breathing in a sub-optimal manner. More particularly, use of the currently available techniques results elevated levels of patient discomfort as the currently available techniques are generally programmed to deliver the backup breath exactly one breath period after the last trigger. Hence, it may be desirable to develop a method configured to enhance delivery of ventilatory support to the patient, thereby reducing patient discomfort and enhancing clinical workflow. More particularly, it may be desirable to develop a method configured to allow smart delivery of backup breaths, thereby allowing the patient 12 to temporarily pause breathing and avoid inadvertent delivery of backup breaths during the pauses in breathing.

Figure 3:
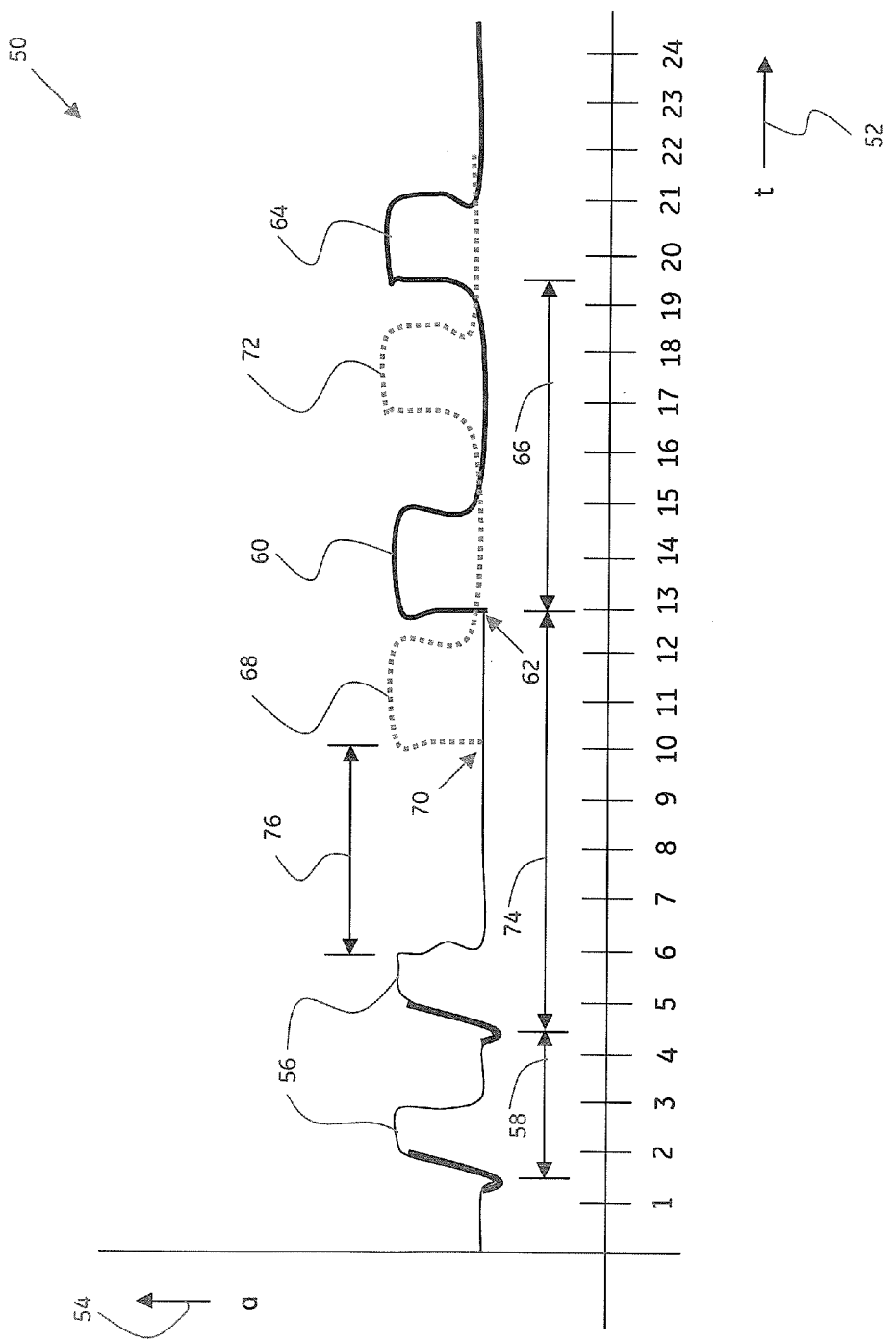
FIG. 3 is a diagrammatic illustration of the method of delivering ventilatory support to a patient of FIG. 2, in accordance with aspects of the present technique.

FIG. 3 is a flow chart 30 depicting an exemplary method for delivering smart ventilatory support to a patient, such as the patient 12 (see FIG. 1). In a presently contemplated configuration, the smart backup breath delivery module 16 (see FIG. 1) may be configured to aid the ICU ventilator 14 (see FIG. 1) in performing the exemplary method for delivering ventilatory support to the patient.

The method starts at step 32 where a breathing pattern of the patient is continually monitored. As will be appreciated, a breathing pattern of a patient, such as the patient 12, under ventilatory support may vary over periods of time. For example, a spontaneously breathing patient may breath in an accelerated fashion and/or slow his/her breathing or even pause breathing. Using currently available techniques, once the ventilation system detects this pause in the breathing of the patient, a backup breath is delivered to the patient as these techniques are programmed to deliver the backup breath exactly one breath period after the last trigger. Moreover, the clinician typically sets the backup rate to a very low value. Unfortunately, a patient that has temporarily paused breathing may get unwanted and/or uncomfortable backup breaths. Hence, it may be desirable to monitor the breathing pattern of the patient, as indicated by step 32.

Further, in accordance with exemplary aspects of the present technique, a method of delivering ventilatory support by controlling delivery of backup breaths to the patient is presented. More particularly, the exemplary method may be configured to facilitate delay in the delivery of backup breaths based upon a previous breath interval, thereby allowing the clinicians to set a more appropriate backup rate.

In accordance with aspects of the present technique, the smart backup breath delivery module 16 may be configured to delay the onset of a first backup breath. More particularly, the smart backup breath delivery module 16 may be configured to delay the onset of the first backup breath based upon a time interval between two consecutive previous breaths or triggers. This time interval may be referred to as a previous breath interval. In other words, the smart backup breath delivery module 16 may be configured to delay the onset of the first backup breath by postponing commencement of the first backup breath based upon the previous breath interval. Accordingly, a time interval between two consecutive breaths may be measured, as depicted by step 34. In certain embodiments, the smart backup breath delivery module may be configured to monitor a "previous" breath interval. As will be appreciated, in a spontaneous breathing mode, the patient triggers all breathing. In other words, a time interval between two previous triggers (breaths) may be monitored, as depicted by step 34.

Traditionally, if the previous breath interval exceeds a predetermined threshold, the first backup breath is delivered. The predetermined threshold may include a user set period of time, in certain embodiments. For example, the user set period of time may include a backup rate. Also, once the patient resumes breathing again, the delivery of backup breaths is stopped. In accordance with aspects of the present technique, the smart backup breath delivery module may be configured to delay the onset of the first backup breath in order to allow the patient to resume breathing after a pause in his/her breathing pattern. Accordingly, at step 36, the previous breath interval may be compared with the predetermined threshold.

Subsequently, at step 38, a check may be carried out to verify if the previous breath interval exceeds the predetermined threshold. If it is verified that the previous breath interval exceeds the predetermined threshold, then the onset of the first backup breath may be delayed, as indicated by step 40. However, at step 38, if it is verified that the previous breath interval does not exceed the predetermined threshold, then control may be returned to step 34.

In accordance with exemplary aspects of the present technique, the onset of a first backup breath may be delayed by up to two times the set backup period. As used herein, the term backup period is used to refer to a reciprocal of the user set backup rate. More particularly, in according to aspects of the present technique, the onset of the first backup breath may be delayed as follows:

$$\text{First backup breath period} = [(\text{Backup period} - \text{Previous breath interval}) + \text{Backup period}] \quad (1)$$

Using equation (1), a first backup period may be computed. As used herein, the term first backup period may be used to refer to a time period between a previous breath trigger and the first backup breath. In other words, the first backup period may be representative of a time period between when the last trigger occurred and when the first backup breath is initiated. The method of delivering ventilatory support of FIG. 2 may be better understood with reference to FIGS. 3-4.

Figure 2:
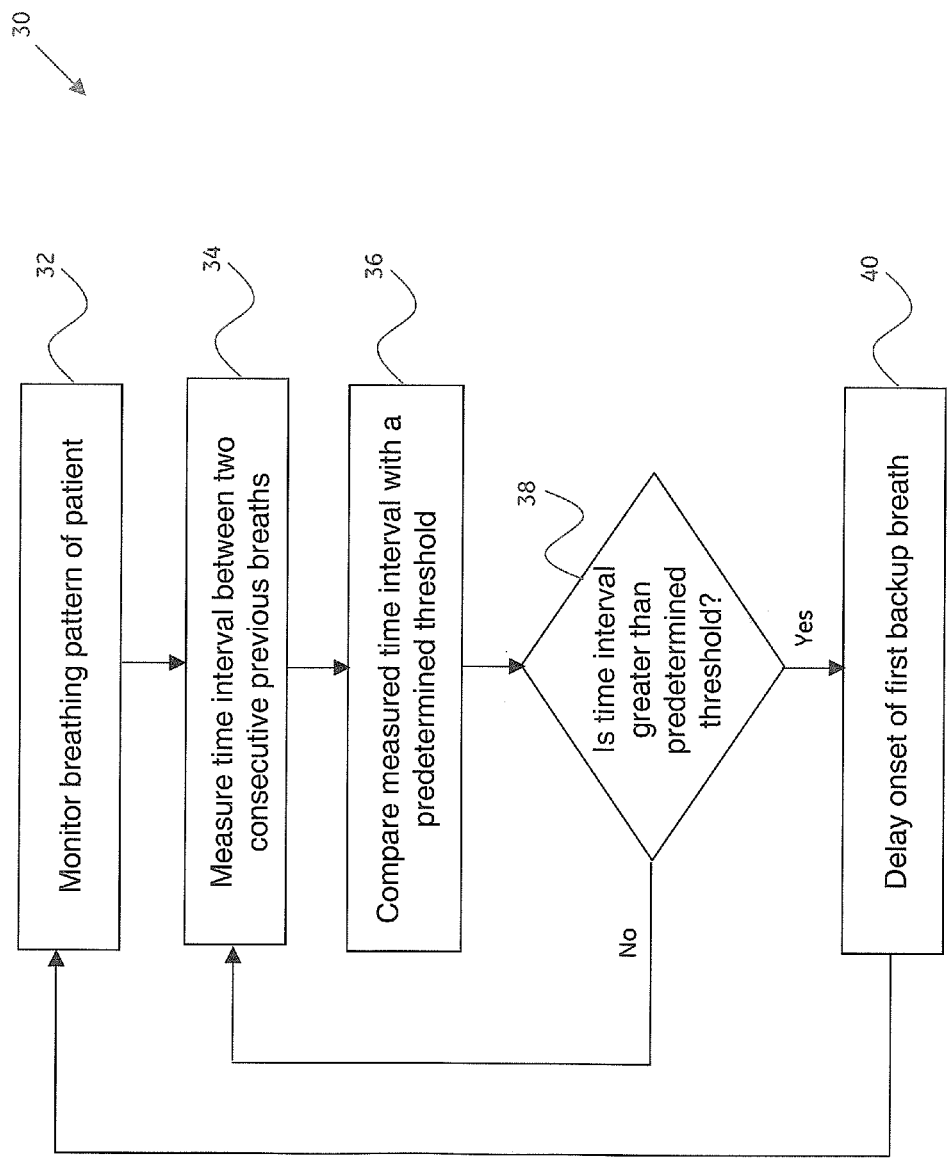
FIG. 2 is a flow chart illustrating an exemplary method of delivering ventilatory support to a patient, in accordance with aspects of the present technique.

Turning now to FIG. 3, a diagrammatic illustration 50 of an exemplary method of delivering ventilatory support of FIG. 2 is illustrated. More particularly, the step of delaying the onset of the first backup breath (step 40 of FIG. 2) is depicted in FIG. 3. Reference numeral 52 may be representative of a time axis (X-axis), while an amplitude axis (Y-axis) may generally be represented by reference numeral 54. As noted with reference to FIG. 2, the breathing pattern of the patient may be monitored. Patient triggered breaths may generally be represented by reference numeral 56.

In the example illustrated in FIG. 3, the breathing pattern of the patient indicates that the patient is breathing twice as fast as a set backup rate and then stops breathing. Furthermore, in the present example, the patient is shown as triggering at 20 breaths per minute (bpm) and then stops breathing. The 20 bpm triggering rate results in a breath period of 3 seconds. This breath period may generally be represented by reference numeral 58 and may be referred to as the previous breath interval.

Furthermore, as previously noted, a time interval between two previous triggers may be measured. In other words, the previous breath interval may be measured. Additionally, in the present example, the previous breath interval is 3 seconds. However, as illustrated in FIG. 3, the patient stops breathing at the $6^{th}$ second. Once the new previous breath interval is computed, the new previous breath interval may be compared with the predetermined threshold, namely the user set backup period. Since the newly computed previous breath interval is greater than the predetermined threshold, the onset of the first backup breath may be delayed, thereby allowing the patient additional time to resume his/her breathing.

It may be noted that in the present example the user set backup rate may be 10 bpm. Consequently, a corresponding backup period may be 6 seconds. Using equation (1), the first backup breath period may be computed as:

$$\text{First backup period} = [(6-3)+6] = 9 \text{ seconds}.$$

Accordingly, the onset of a first delayed backup breath may be delayed to be initiated at the $13^{th}$ second. In the present example, the first delayed backup breath may be represented by reference numeral 60. The time of onset of the first delayed backup breath may be represented by reference numeral 62. Also, reference numeral 64 may be representative of a second delayed backup breath. It may be noted that the second delayed backup breath 64 is configured to occur in accordance with a user set backup period 66. In other words, once the first delayed backup breath 60 is delivered, subsequent backup breaths, such as the second delayed backup breath 64, may be delivered at the preset backup period 66 until the patient resumes breathing.

It may be noted that use of currently available techniques results in a first backup breath 68 occurring at exactly one time period after the last trigger. In other words, in the present example, the first backup breath may have occurred at 6 seconds after the last trigger that occurs at the $4^{th}$ second. In other words, the first backup breath 68 may have occurred at the $10^{th}$ second. The onset of the first backup period 68 may be represented by reference numeral 70. Furthermore, reference numeral 72 is representative of a second backup breath that may have occurred after a set backup period after the occurrence of the first backup breath 68. It may be noted that if the pause in breathing exceeds the apnea time, the first backup breath will be delivered.

In the present example, by implementing the method for delivering ventilatory support by delaying the onset of the first delayed backup breath 60, the time interval between the last trigger at the $4^{th}$ second and the onset of the first delayed backup breath 60 may advantageously be enhanced to 9 seconds as opposed to a time interval of 6 seconds with use of the currently available techniques. The time period between the last trigger 56 at the $4^{th}$ second and the first delayed backup breath 60 may generally be represented by reference numeral 74. Similarly, reference numeral 76 may be indicative of a time period between the last trigger 56 at the $4^{th}$ second and the first backup breath 68 as delivered by the presently available techniques. Consequently, the patient may be permitted to momentarily pause his/her breathing without the ventilation system prematurely delivering a backup breath and causing patient discomfort.

Figure 4:
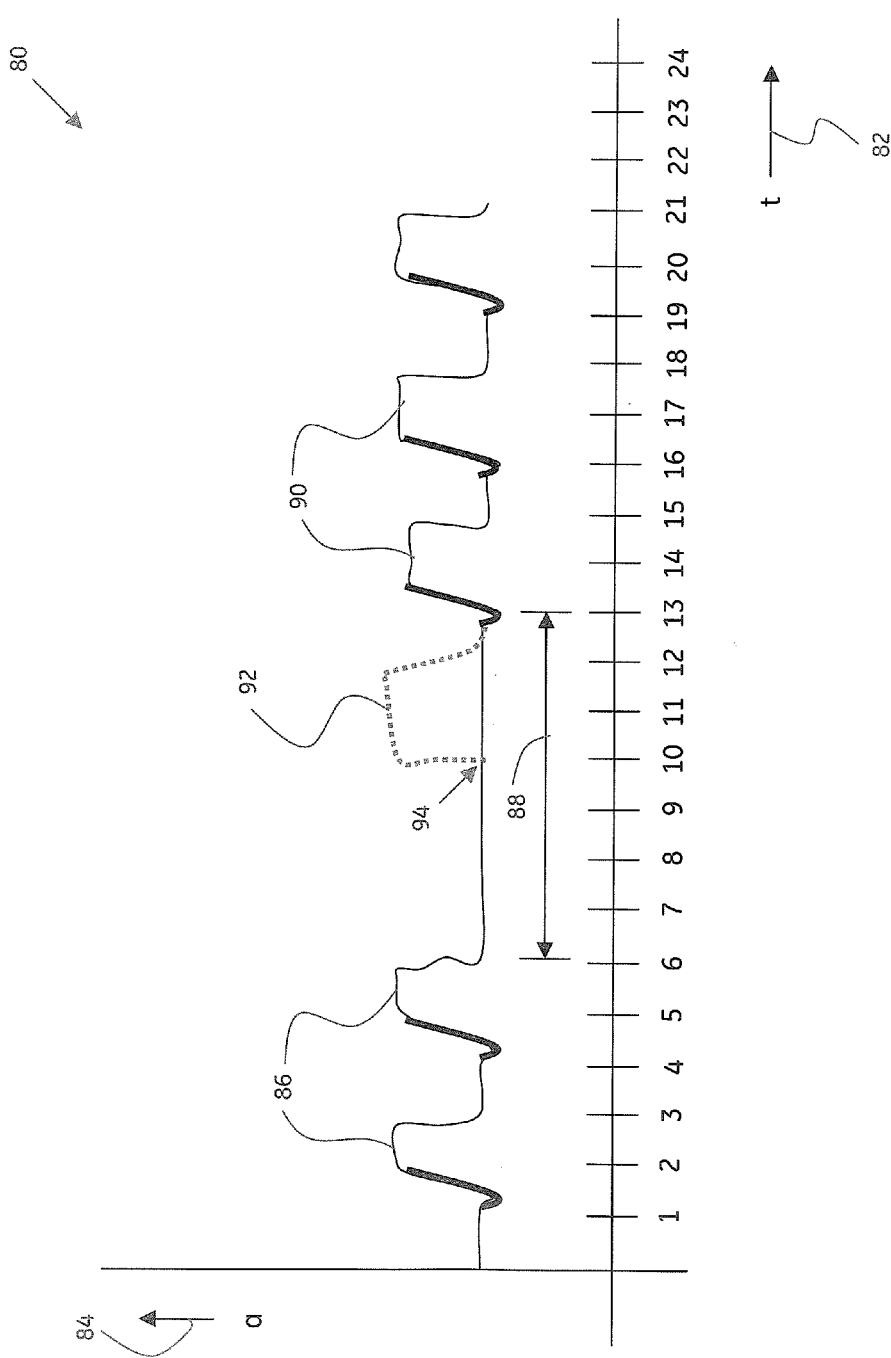
FIG. 4 is another diagrammatic illustration of the method of delivering ventilatory support to a patient of FIG. 2, in accordance with aspects of the present technique.

Referring now to FIG. 4, a diagrammatic illustration 80 of an exemplary method of delivering ventilatory support of FIG. 2 is illustrated. More particularly, the step of delaying the onset of the first backup breath (step 40 of FIG. 2) is depicted in FIG. 4. Reference numeral 82 may be representative of a time axis (X-axis), while an amplitude axis (Y-axis) may generally be represented by reference numeral 84. As noted with reference to FIG. 2, the breathing pattern of the patient may be monitored. Patient triggered breaths may generally be represented by reference numeral 86.

Here again, in the example illustrated in FIG. 4, the breathing pattern of the patient indicates that the patient is breathing twice as fast as a set backup rate and then pauses breathing. Furthermore, in the present example, the patient is shown as triggering at 20 breaths per minute (bpm) and then pauses breathing for 9 seconds. The 20 bpm triggering rate results in a breath period of 3 seconds. This breath period may generally be represented by reference numeral 58.

Furthermore, as previously noted, a time interval (the previous breath interval) between two previous triggers 86 may be measured. In the present example, the previous breath interval between the previous two triggers 86 is 3 seconds. However, as illustrated in FIG. 3, the patient pauses breathing at the $6^{th}$ second and resumes breathing at the $13^{th}$ second. The resumed patient triggered breaths may generally be represented by reference numeral 90. Accordingly, a new previous breath interval may be computed. Once the new previous breath interval is computed, the new previous breath interval may be compared with the predetermined threshold, namely the user set backup period. In the present example, the new previous breath interval is 9 seconds, while the predetermined threshold (set backup period) is 6 seconds. Since the new previous breath interval is greater than the predetermined threshold, the onset of the first backup breath may be delayed.

In the present example, it may be noted that the user set backup rate may be 10 bpm. Consequently, a corresponding period may be 6 seconds. Using equation (1), the first backup breath period may be computed as:

First backup period=[(6−3)+6]=9 seconds.

Accordingly, the onset of a first delayed backup breath may be delayed to be initiated at the $13^{th}$ second. However, since the patient is shown as resuming breathing at the $13^{th}$ second, the delayed first backup breath is not delivered to the patient.

It may be noted that use of currently available techniques may have resulted in a first backup breath 92 occurring at exactly one time period after the last trigger. In other words, in the present example, the first backup breath may have occurred 6 seconds after the last trigger that occurs at the $4^{th}$ second. In other words, the first backup breath 92 may have occurred at the $10^{th}$ second. This onset of the first backup breath 92 may be indicated by reference numeral 94.

By implementing the method for delivering ventilatory support by delaying the onset of the first backup breath as described with reference to FIG. 4, the patient may be permitted to rest or pause up to 2 breath periods before a backup breath is delivered. Consequently, the patient is permitted to pause in his/her breathing without the ventilation system prematurely delivering a backup breath and causing patient discomfort. In other words, the present technique may be configured to prevent a first backup breath from occurring during a pause in the patient's breathing. In contrast, using the currently available technique, the first backup breath may have occurred at the $10^{th}$ second, thereby delivering unwanted backup breaths to the patient. Moreover, the present technique allows the clinician to set a relatively higher backup rate and hence enhance patient comfort.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java or in paradigms like Service Oriented Architecture. Such code, as will be appreciated by those of ordinary skill in the art, may be stored or adapted for storage on one or more tangible, machine readable media, such as on memory chips, local or remote hard disks, optical disks (that is, CDs or DVDs), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The method for delivering ventilatory support to the patient and the system for delivering ventilatory support to the patient described hereinabove dramatically simplify clinical workflow by advantageously allowing control of delivery of the first backup breath. More particularly, patient comfort may be dramatically enhanced by delaying the onset of the first backup breath, thereby allowing the patient to temporarily pause breathing. Furthermore, employing the exemplary method for delivering ventilatory support advantageously allows the patient to pause breathing without having the ventilation system prematurely delivering an unwanted backup breath. In addition, the smart delivery of backup breaths described hereinabove enables the clinician to set a more appropriate backup rate.

The above-description of the embodiments of the system for delivering ventilatory support to the patient and the method for delivering ventilatory support to the patient have the technical effect of enhancing patient comfort by allowing the patient to temporarily pause breathing by delaying onset of backup breaths. Additionally, allowing the clinician to set a higher backup rate may enhance clinical workflow.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for delivering ventilatory support to a patient, the method comprising:
monitoring a breathing pattern of the patient;
controlling with a ventilation system delivery of a first backup breath;
delaying onset of the first backup breath; and
measuring a single time interval between two consecutive previous breaths, wherein delaying the onset of the first backup breath comprises postponing commencement of the first backup breath, wherein the delay includes the measured single time interval and a backup period, wherein the backup period is inversely proportional to a user-selected backup rate.

2. The method of claim 1, wherein the patient is operationally coupled to the ventilation system.

3. The method of claim 2, wherein the patient is operationally coupled to the ventilation system via an invasive interface, a non-invasive interface, or a combination thereof.

4. The method of claim 1, further comprising comparing the measured single time interval with a predetermined threshold.

5. The method of claim 4, wherein the predetermined threshold comprises a pre-determined backup rate.

6. The method of claim 4, further comprising delaying the onset of the first backup breath if the measured single time interval exceeds the predetermined threshold.

7. The method of claim 5, wherein postponing commencement of the first backup breath comprises delaying the onset of the first backup breath by up to two times the predetermined threshold.

8. A system for delivering ventilatory support to a patient, the system comprising:

a ventilation system that provides artificial respiration to the patient, wherein the ventilation system is configured to be operationally coupled to the patient via a patient interface; and a backup breath delivery module that monitors a breathing pattern of the patient and automatically controls delivery of a first backup breath by delaying onset of the first backup breath, wherein the backup breath delivery module further:

measures a single time interval between two consecutive previous breaths;

compares the single time interval with a predetermined threshold; and postpones commencement of the first backup breath, wherein the delay includes the measured single time interval and a backup period, wherein the backup period is inversely proportional to a user-selected backup rate.

9. The system for delivering ventilatory support to a patient of claim 8, wherein the backup breath delivery module is configured to postpone commencement of the first backup breath by delaying onset of the first backup breath by up to two times a predetermined threshold.

10. A computer readable medium comprising one or more tangible media, wherein the one or more tangible media comprise:

code adapted to monitor a breathing pattern of the patient;

code adapted to control delivery of a first backup breath by delaying onset of the first backup breath; and code adapted to measure a single time interval between two consecutive previous breaths, wherein the code adapted to delay the onset of the first backup breath comprises code adapted to postpone commencement of the first backup breath, wherein the delay includes the measured single time interval and a backup period, wherein the backup period is inversely proportional to a user-selected backup rate.

11. The computer readable medium, as recited in claim 10, further comprising code adapted to compare the measured single time interval with a predetermined threshold.

12. The computer readable medium, as recited in claim 11, further comprising code adapted to delay the onset of the first backup breath if the measured single time interval exceeds the predetermined threshold.

13. The computer readable medium, as recited in claim 11, wherein code adapted to postpone commencement of the first backup breath comprises code adapted to delay the onset of the first backup breath by up to two times the predetermined threshold.

* * * * *